United States Patent [19]

Breidegam

[11] Patent Number: 4,782,425
[45] Date of Patent: Nov. 1, 1988

[54] CONDUCTIVE ELASTIC STRAP CLOSURE

[75] Inventor: Albert C. Breidegam, Sharpsburg, Ga.

[73] Assignee: Semtronics Corporation, Peachtree City, Ga.

[21] Appl. No.: 6,467

[22] Filed: Jan. 23, 1987

Related U.S. Application Data

[63] Continuation-in-part of Ser. No. 804,052, Dec. 2, 1985, Pat. No. 4,639,825, which is a continuation-in-part of Ser. No. 654,636, Sep. 25, 1984, Pat. No. 4,577,256.

[51] Int. Cl.$^4$ .............................................. H05F 3/02
[52] U.S. Cl. ........................................ 361/212; 24/170
[58] Field of Search .................. 361/212, 220; 24/170, 24/191

[56] References Cited

U.S. PATENT DOCUMENTS

| | | | |
|---|---|---|---|
| 1,531,862 | 3/1925 | Larned | 273/73 D |
| 3,063,447 | 11/1962 | Kirsten | 128/134 |
| 3,377,509 | 4/1968 | Legge | 361/220 |
| 3,422,460 | 1/1969 | Burke et al. | 2/73 |
| 3,424,698 | 1/1969 | Lupinski et al. | 252/500 |
| 3,459,997 | 8/1969 | Legge | 361/ |
| 3,541,389 | 11/1970 | Van Name | 317/2 |
| 3,582,448 | 6/1971 | Okuhasi | 161/87 |
| 3,596,134 | 7/1971 | Burke | 361/220 |
| 3,699,590 | 10/1972 | Webber et al. | 2/73 |
| 3,812,861 | 5/1974 | Peters | 361/220 X |
| 3,832,841 | 9/1974 | Cole | 57/152 |
| 3,851,456 | 12/1974 | Hamada et al. | 57/140 |
| 3,857,397 | 12/1974 | Brosseau | 361/220 X |
| 3,904,929 | 9/1975 | Kanaya et al. | 317/2 |
| 3,949,129 | 4/1976 | Hubbard | 428/190 |
| 3,986,530 | 10/1976 | Maekawa | 139/425 |
| 3,987,613 | 10/1976 | Woods et al. | 57/140 |
| 4,267,233 | 5/1981 | Tanaka et al. | 428/389 |
| 4,321,789 | 3/1982 | Dammann et al. | 57/224 |
| 4,373,175 | 2/1983 | Mykkanen | 361/212 X |
| 4,398,277 | 8/1983 | Christiansen et al. | 361/212 X |
| 4,402,560 | 9/1983 | Swainbank | 339/11 |
| 4,420,529 | 12/1983 | Westhead | 428/244 |
| 4,422,483 | 12/1983 | Zins | 139/420 |
| 4,459,633 | 7/1984 | Vandemark | 361/220 |
| 4,475,141 | 10/1984 | Antonevich | 361/220 |
| 4,577,256 | 3/1986 | Breidegam | 361/212 X |
| 4,605,984 | 8/1986 | Fiedler | 361/220 |
| 4,639,825 | 1/1987 | Breidegam | 361/212 |
| 4,662,695 | 5/1987 | Gordon et al. | 361/220 X |
| 4,664,158 | 5/1987 | Sands | 139/422 |

FOREIGN PATENT DOCUMENTS 2547390 5/1977 Fed. Rep. of Germany.
1067260 8/1965 United Kingdom.

Primary Examiner—L. T. Hix
Assistant Examiner—Brian W. Brown
Attorney, Agent, or Firm—Kilpatrick & Cody

[57] ABSTRACT

Clasps for conductive grounding straps. Clasps according to the present invention allow the strap material to exit the clasp with its conductive side facing the wearer rather than being exposed. The resulting closure decreases the possibility of accidental contact of conductive sections of the strap with high voltage or other dangerous electrical potential that can result in injury or death to the wearer. Because the material exits the clasp with its conductive side not exposed, the free position of the material extending beyond the clasp need not be cut for safety reasons. The strap may thus be adjusted to accomodate various wrist sizes and be used by various wearers.

17 Claims, 2 Drawing Sheets

CONDUCTIVE ELASTIC STRAP CLOSURE

This is a continuation-in-part of my application Ser. No. 804,052 filed Dec. 2, 1985, U.S. Pat. No. 4,639,825 issued Jan. 27, 1987 entitled STRETCHABLE GROUNDING STRAP HAVING REDUNDANT CONDUCTIVE SECTIONS, which is a continuation-in-part of my application Ser. No. 654,636 filed Sept. 25, 1984, now U.S. Pat. No. 4,577,256 issued Mar. 18, 1986 entitled WOVEN STRETCHABLE GROUNDING STRAP.

BACKGROUND OF THE INVENTION

This invention relates to closures or clasps for securing conductive grounding straps about the wrist or limb.

Static electricity causes problems for electronics manufacturers and those in other industries, particularly with the advent of integrated circuits and other microelectronic components. Components such as integrated circuits, for instance, may be disabled or destroyed by over-voltages or power density resulting from static electricity. Certain junctions in such circuits can be destroyed by as little as a 50-volt potential, which radically changes the doping structure in their lattices. Power densities resulting from excessive potential and imperfections in circuit layout or structure can vaporize or radically alter the silicon substrate and thus impair or destroy a circuit's performance. Yet a person walking on a carpet on a dry day can accumulate as much as 30,000 volts of potential, and he can triboelectrically generate thousands of volts by simply changing his position in his chair or handling a styrofoam cup.

Such a person can inadvertently discharge such static electric potential into the circuit or component by touching it and causing over-voltage or excessive power density. Additionally, the potential in such a person's body can induce a charge in a circuit that can later cause over-voltage or excessive power density when the circuit is subsequently grounded.

More and more frequently, therefore, those in industries in which integrated circuits and other microelectronic components are handled or assembled are taking measures to limit the failure rate of those circuits and components by attempting to keep them as well as their environment at zero electrical potential. Such measures include providing workers and work stations with anti-static carpet, conductive or dissipative grounded desk top work surfaces, hot air ion generators which emit ions to neutralize static charges, and grounding straps to keep workers at zero potential. The term "conductive" herein, and according to its customary usage in the art, means an electrical resistance of between zero and $10^5$ ohms. Similarly, "dissipative" means a resistance of between $10^5$ and $10^9$ ohms, "anti-static" means a resistance of between $10^9$ and $10^{14}$ ohms, and "insulative" means a resistance of more than $10^{14}$ ohms.

A grounding strap must have several features in order to perform its grounding function effectively. First, it must ensure that the wearer's skin is electrically connected to ground. This connection is typically accomplished by a conductive surface on the inside of the strap contacting the skin. The conductive surface is electrically connected to a grounding cord which leads from the strap to a grounded electrical connection. If the electrical contacting means on the inside of the strap becomes dirty or fouled by oil, perspiration or hair, the strap may lose its effectiveness. It is therefore important to use a conductive material on the inner surface of the strap that does not easily become dirty or fouled.

Second, comfort is a premium consideration, because if the strap is uncomfortable, the wearer will be tempted to remove it and can thereby cause damage to electrical components on which he is working. A strap that is easily stretchable, that breathes, that is attractive and that poses minimum inconvenience to the wearer is therefore highly desired.

The situations in which grounding wrist straps are used heightens the importance of their being comfortable so that they are continuously worn and maintain continuous electrical contact with the skin. A person working on microelectronic components or integrated circuits may be completely unaware that he has accumulated minor static electrical charges and he may therefore unwittingly be in a position to disable circuits on which he is working or which he is handling. If his strap is loose or he has removed it, he may be unaware that electrical discharges transmitted from his fingers are disabling these circuits. (A typical person cannot sense a static electrical discharge of less than approximately 3,500 volts.) No one may discover that the circuits have been disabled or damaged until hours, days or weeks later, when the circuits have been placed in components or devices which fail in the field. Removal and repair or replacement of these circuits once in the field is far costlier than avoiding potential failure while the wearer is handling the circuits. Thus, the wearer's employer typically must depend upon the effectiveness of the wrist strap to maintain a lower failure rate of such electronic circuits and components, by maintaining continuous electrical contact with the wearer's wrist and by providing him minimum temptation to remove the strap from his wrist.

Several approaches have been followed in an attempt to address these considerations. An extensible metal band similar to a Speidel ® watchband, for instance, is disclosed in U.S. Pat. No. 4,373,175 issued Feb. 8, 1983 to Mykkanen. A strap made of an outer and inner conductive polyolefin layer which sandwich an intermediate nylon scrim layer is disclosed in U.S. Pat. No. 3,857,397 issued Dec. 31, 1984 to Brosseau. That patent shows the use of hook and loop fastening material to hold the strap adjustably on the wrist.

A knitted stretchable fabric strap containing stainless steel fibers is disclosed in U.S. Pat. No. 4,398,277 issued Aug. 9, 1983 to Christiansen and Westberg. The knitted fabric material of the strap is perhaps cooler and lighter than the metal or plastic straps mentioned above, but a plastic and metal fitting permanently closes the strap into a loop of predetermined size. The wearer thus cannot adjust the strap to improve electrical contact or to reduce constriction about the wrist.

My U.S. Pat. No. 4,577,256 issued Mar. 18, 1986 entitled WOVEN STRETCHABLE GROUNDING STRAP and mentioned above discloses a fabric strap that has an adjustable closure or clasp. That patent is incorporated herein by reference. The clasp avoids the need to manufacture two or more models of the strap for different size wrists. It also makes the strap markedly more comfortable and effective for all sizes of wrists. The closure reduces the wearer's temptation to remove the strap and thus reduces the chance that circuits and components will be damaged by the wearer's static charges.

My adjustable clasp mentioned above includes a fastener for connection to a grounding cord. The fastener passes through the clasp's body and is electrically and physically connected to a metallic plate. The metallic plate contacts the wearer's wrist or limb as well as conductive yarns on the inner surface of the conductive elastic material of the strap.

Because the fastener passes from the outer to the inner surface of the clasp body, it prevents the possibility of the conductive elastic material being threaded through the strap from one end to the other. The loose end of the material to be secured by the clasp thus enters the clasp body from the end of the clasp opposite the fastener. The material is secured by a pivotally mounted gate and then exits the clasp on the clasp's top surface. The conductive yarns of the material as a result are exposed. To reduce the possibility of accidental contact with dangerous electrical potential, the material extending beyond the top of the clasp body is typically cut after the strap is adjusted to fit the wearer's wrist. Once cut, the strap obviously cannot be adjusted to accommodate larger wrist sizes.

SUMMARY OF THE INVENTION

The clasps of the present invention allow the conductive grounding strap material to pass through the clasp body and exit the body so that the conductive yarns of the free end of the material face toward the wrist rather than being exposed. The clasp body includes a passageway through which the conductive elastic material passes. A gate adjustably secures the material into place. One end of the material is attached to the gate end of the clasp body and the other end of the material exits the clasp body in the same direction. The conductive elastic fibers of the material are connected to a grounding cord fastener or fasteners on the clasp's top surface by conductive fittings which may be shaped metal plates that physically connect the conductive yarns and the fasteners and also provide surface contact with the wearer's skin, but which do not obstruct passage of the conductive elastic material through the clasp body.

The clasps of the present invention avoid the need to break the electrical connection between the grounding cord fastener and the conductive section of the strap as the strap is being placed on the wrist. Although it may be possible to design a clasp which has a top door that opens in order to admit the loose end of strap material through the clasp, such a design would likely require that electrical connection between the grounding cord fastener and the conductive sections of the material be broken when the clasp is donned. Electrical contact would likely have to be established by moving parts such as electrical contacts biased against one another, one for the grounding cord fastener and one for the conductive section. This arrangement would introduce a site of potential failure into the strap, as the contacts became bent or fouled by dirt, body oil or other foreign substances.

Clasps may be made according to the present invention to accommodate material having two or more conductive sections such as the material disclosed in my U.S. Pat. No. 4,639,825 issued Jan. 27, 1987 entitled STRETCHABLE GROUNDING STRAP HAVING REDUNDANT CONDUCTIVE SECTIONS, which is incorporated by this reference. Such straps are useful, among other reasons, because they allow circuitry to monitor the electrical connection between the wearer and ground.

Clasps according to the present invention are also equally useful for woven and knitted fabric material as well as any other flexible material which is suitable for use in conductive grounding straps.

It is therefore an object of the present invention to provide a conductive grounding strap clasp that increases the safety of the wearer by allowing the conductive material to exit the clasp body with its conductive side facing the wearer rather than being exposed.

It is an additional object of the present invention to provide a conductive grounding strap clasp that allows the strap to be adjustable and to accommodate the wrists of various wearers by not requiring that the material of the strap be cut when fitted to avoid exposure of conductive yarns.

It is an additional object of the present invention to provide an inexpensive, versatile and attractive closure that increases the comfort and effectiveness of the conductive grounding strap with which it is used.

It is an additional object of the present invention to provide a conductive grounding strap clasp that allows the grounding cord fastener to be electrically connected with its corresponding conductive section of the strap material at all times and thus minimize the possibility of failure of that electrical connection.

Other objects, features and advantages of this invention will be apparent in the specification, claims and drawings.

BRIEF DESCRIPTION OF THE DRAWINGS

FIG. 4b is an exploded perspective view of a third embodiment of a conductive elastic strap clasp according to the present invention that accommodates material having two conductive sections but includes conductive fittings different than those of the clasp of FIG. 4a.

DETAILED DESCRIPTION OF THE DRAWINGS

Figures 1, 2:
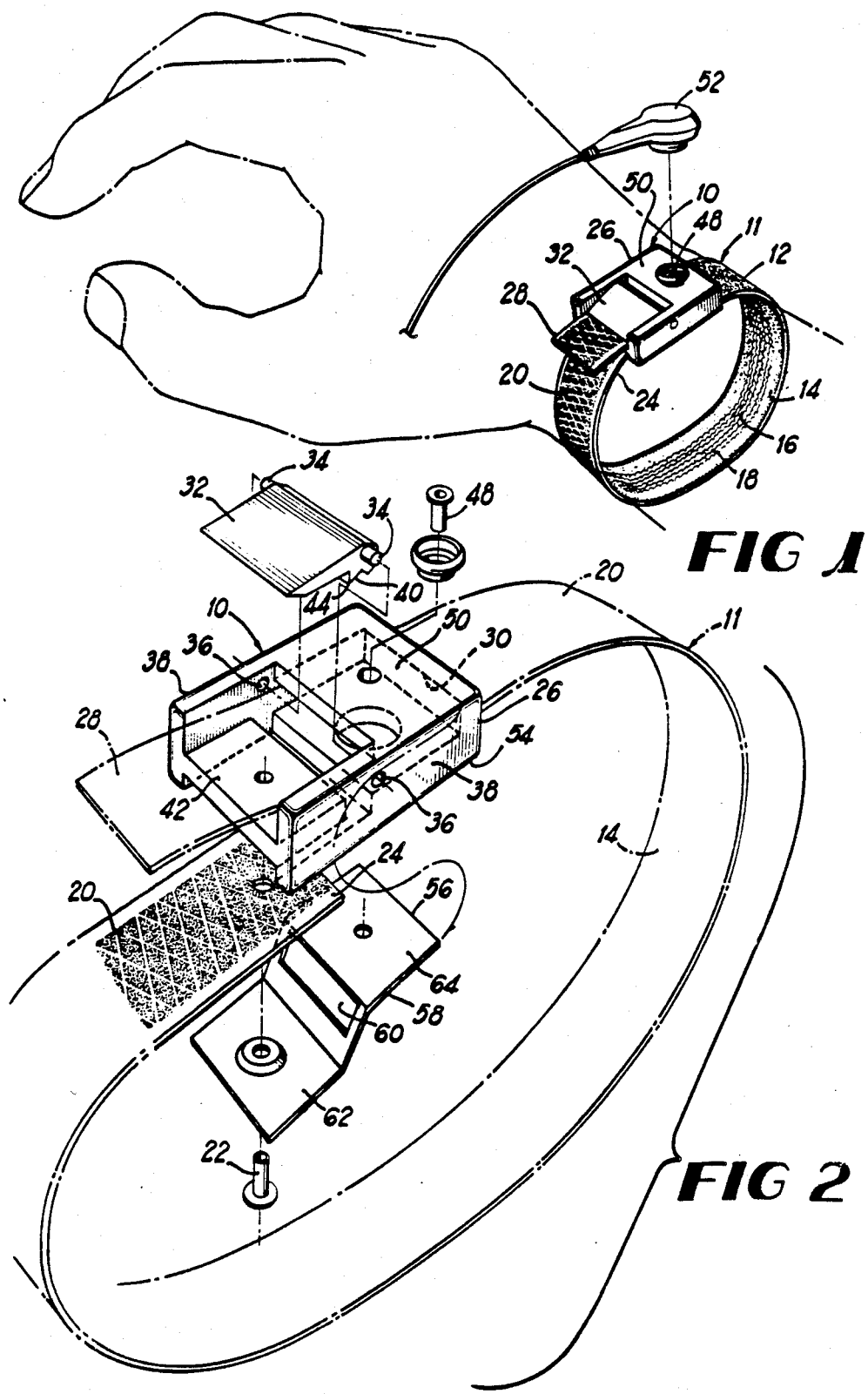
FIG. 1 is a perspective view of a conductive grounding strap clasp according to the present invention.
FIG. 2 is an exploded perspective view of the clasp shown in FIG. 1.

FIG. 1 illustrates a preferred embodiment of a clasp 10 of grounding strap 11 that utilizes conductive elastic material 12. Clasp 10 should be made of antistatic material to minimize risk of inadvertent electrical contact with an electrical power source and subsequent electrocution of the wearer, while simultaneously avoiding undesired generation of static electricity on the clasp that could occur if the clasp were made of insulative material. Yet clasp 10 should be made of material hard enough to capture material 12 firmly and resilient enough to be sufficiently durable. In the preferred embodiment, clasp 10 is of nylon, which because of its hygroscopic properties is anti-static, but other suitable polymeric or other materials may be used.

The inner surface 14 of material 12 in this drawing, the surface facing the wearer's limb, includes a section 16 of conductive yarns 18 which are woven or knitted into the inner surface 14 of material 12 but are not exposed on outer surface 20. Exposure of yarns 18 on outer surface 20 would provide a conductive surface that could accidentally contact a high voltage source or other dangerous potential and possibly electrocute the wearer. Material 12 may be woven or knitted fabric or it may be formed of plastic or polymeric layers which include carbon synthetic material or other appropriate material for conductivity. Any other flexible material, elastic or inelastic, is appropriate for clasp 10 of the present invention. Material having only one conductive surface is preferred in order to realize the safety advantages of clasp 10 but material that is conductive on both sides may also be used.

A connection means 22 connects a first end 24 of material 12 to clasp body 26. Connection means 22 may be a rivet, screw, staple, eyelet or other appropriate connector or fastener. It is a rivet in the preferred embodiment shown in FIG. 1.

Second end 28 of material 12 is the end that is adjustably secured to clasp 10 to secure strap 11 about the wearer's wrist or limb. Second end 28 is threaded into passageway 30 as shown in FIG. 1 and in cross-section in FIG. 3. Passageway 30 extends longitudinally from one end of clasp body 26 to gate 32 located toward the other end of clasp body 26. Gate 32 is a plate-like member which has an essentially J-shaped cross-section and which is pivotally mounted to clasp body 26 by pins 34 formed at the foot of the "J." These pins 34 are inserted into pinholes 36 in the side walls 38 of clasp body 26. The portion of gate 32 corresponding to the shorter lip of the "J" is a jam 40 which forces second end 28 of material 12 against the bottom wall 42 of clasp body 26 when gate 32 is pressed closed. Gate 32 is held in position as jam 40 passes beyond vertical with respect to bottom surface 42 of clasp body 26 and thus into an over-center relationship. Jam 40 may have teeth to allow it to grip more tightly second end 28 of material 12.

Figure 3:
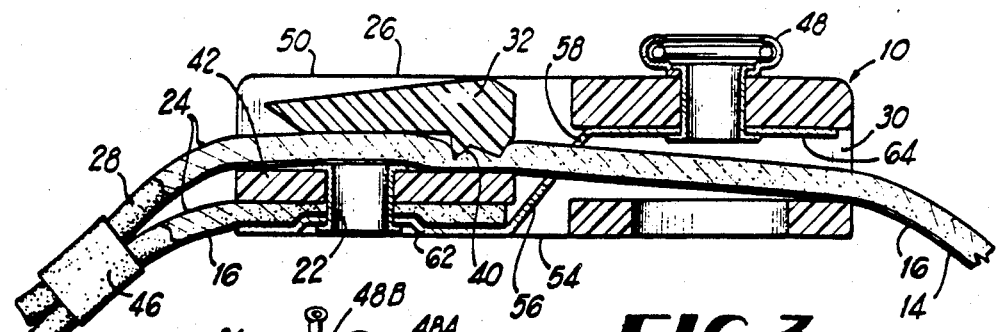
FIG. 3 is a cross-sectional view of the clasp shown in FIG. 1.

FIGS. 1-3 illustrate that second end 28 of material 12 exits clasp body 26 in essentially the same direction as the direction first end of material 24 extends from clasp body 26 so that the conductive inner surface 14 of second end 28 faces first end 24 and the wearer and conductive sections 16 are not exposed to the exterior of strap 11.

Second end 28 of material 12 may be held in place by a loop 46 or other appropriate device to restrain it from flapping or moving freely.

A fastener 48 is physically attached to the top surface 50 of clasp body 26. Fastener 48 receives a grounding cord 52 for connection to the electrical ground. Fastener 48 must be connected to conductive sections 16 of material 12. It is also preferably connected to a metallic plate on the bottom surface 54 of clasp body 26 to increase the effectiveness of strap 11 in ensuring electrical contact between the wearer's skin and ground. Such connection is provided by conductive fitting 56. Conductive fitting 56 may be any conductive element which physically and electrically connects fastener 48 and sections 16 such as, for instance, wires or other metallic elements. It can be a metallic plate 58 having an essentially S-shaped cross-section as shown in FIGS. 2-3. The middle portion of the "S" contains a hole 60 through which material 12 may pass. Bottom leg 62 acts as a plate exposed on bottom surface 54 of clasp body 26 for contacting the wearer's skin while top leg 64 is attached to fastener 48. Bottom leg 62 as shown perhaps best in FIG. 3 is attached by connection means 22 to conductive section 16 of material 12 and bottom wall 42 of clasp body 26. Other arrangements which accomplish this purpose can easily be imagined and would also be appropriate.

The wearer simply inserts second end 28 of material 12 into passageway 30, pulls it beyond gate 32 and presses gate 32 into place. He or she then snaps grounding cord 52 into place on fastener 48 and ensures that grounding cord 52 is connected to electrical ground.

Figure 4A:
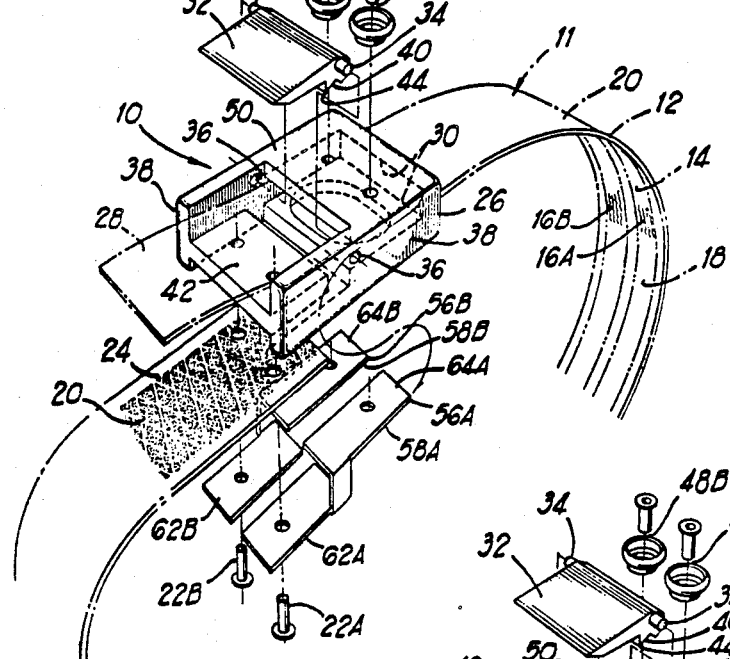
FIG. 4a is an exploded perspective view of a second embodiment of a clasp according to the present invention which accommodates material having two conductive sections.

A second embodiment of the invention is shown in FIG. 4A. This embodiment accommodates straps 11 having two or more sections 16 of conductive elastic material 12. The version shown in FIG. 4A is for straps 11 having two sections 16A and 16B. Connection means 22A and 22B are mounted on bottom wall 42 of clasp body 26 and are electrically connected to a corresponding conductive section 16A and 16B respectively. Each connection means 22A and 22B preferably, but not necessarily, assists in connecting first end of material 24 to clasp body 26. Corresponding fastners 48A and 48B receive grounding cords 52A and 52B so that each section 16A and 16B of conductive elastic material 12 may independently be connected to ground. Any appropriate conductive fittings 56A and 56B may connect fastners 48A and 48B to the conductive sections 16A and 16B of material 12, including wire or other metallic elements. In the embodiment shown in FIG. 4A, conductive fittings 56A and 56B are stamped metal plates having essentially S-shaped cross-sections with part of the middle portion removed so as not to obstruct second end 28 of material 12 as it passes through passageway 30. Conductive fittings 56A and 56B of FIG. 4B are stamped metal plates bent to form a void through which second end 28 of material 12 may pass.

Figure 4B:
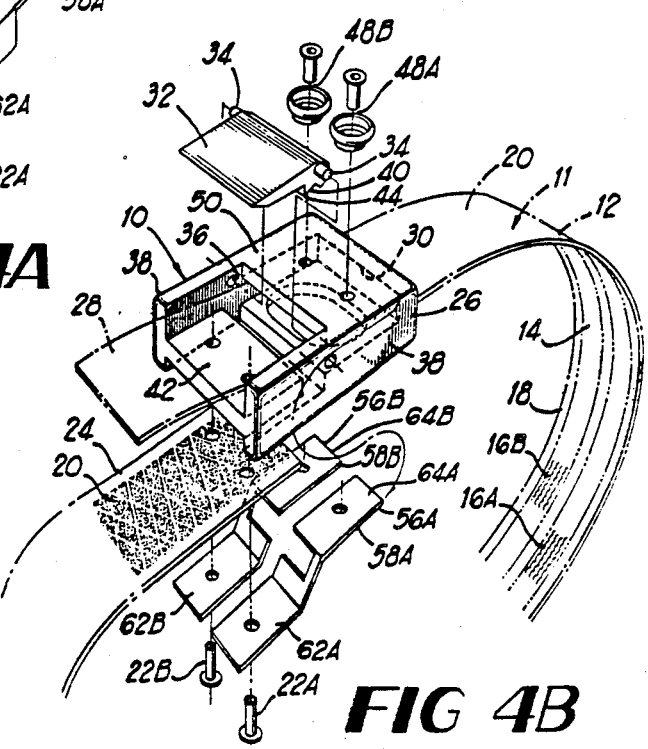

The straps of FIGS. 4A and 4B are used in a manner similar to that of the straps of FIGS. 1-3. Monitoring devices, which are not shown, can detect if either of sections 16 is not connected to the wearer or to ground.

The foregoing description of this invention is for purposes of explanation and illustration. It will be apparent to those skilled in the relevant art that modifications and changes may be made to the invention as thus described without departing from its scope and spirit.

I claim:

1. A clasp for a conductive grounding strap, comprising:
   (a) a clasp body;
   (b) connection means attached to the clasp body for connecting a first end of a length of material having at least one conductive section to the clasp body which connection means is electrically connected to the conductive section of the material;
   (c) a grounding cord fastener attached to the clasp body;
   (d) a passageway formed in the body through which portions of the material may extend;
   (e) a gate means pivotally connected to the body and which is openable and closeable to obstruct the passageway adjustably for adjustably securing a second end of the material in the body so that the second end exits the clasp to overlay the first end; and
   (f) a conductive fitting electrically connecting the fastener and the connection means so that the fastener is electrically connected at all times to the conductive section of the material, regardless of whether the gate means is opened or closed.

2. A clasp according to claim 1 in which the gate means includes a jamb for clamping the second end of material when the gate mans is closed.

3. A clasp according to claim 1 in which the conductive fitting is exposed on the inner side of the clasp body so that the fitting may contact the wearer's skin.

4. A clasp according to claim 1 in which the fastener comprises a snap rivetted to the clasp body.

5. A clasp for a conductive grounding strpa having material which includes an electrically conductive section on one side, comprising:
   (a) a clasp body;
   (b) connection means attached to the clasp body for connecting a first end of a length of material to the clasp body, which connection means is electrically connected to the conductive section;
   (c) a grounding cord fastener attached to the clasp body;
   (d) a passageway formed in the body through which portions of the material may extend;
   (e) a gate means pivotally connected to the body and which is openable and closeable to obstruct the passageway adjustably for adjustably securing a second end of the material in the body so that the second end exits the body with its conductive side facing the first end of material; and
   (f) a conductive fitting electrically connecting the fastener and the connection means so that the fastener is electrically connected at all times to the conductive section of the material, regardless of whether the gate means is opened or closed.

6. A clasp according to claim 5 in which the gate means includes a jamb for clamping the second end of material into place when the gate means is closed.

7. A clasp according to claim 5 in which the conductive fitting is exposed on the inner side of the clasp body so that the fitting may contact the wearer's skin.

8. A clasp for a conductive grounding strap formed of material having at least two conductive sections, comprising:
   (a) a body;
   (b) at least two connection means, at least one of which is for connecting a first end of the material to the clasp body;
   (c) at least two grounding cord fasteners attached to the clasp body, each of which is electrically connected at all times to a conductive section of the material;
   (d) a passageway formed in the body through which portions of the material may extend; and
   (e) a gate means for adjustably securing a second end of the material in the body so that the second end exits the clasp to overlay the first end.

9. A clasp according to claim 8 in which each connection means is electrically connected to a corresponding conductive section of the material and which clasp further comprises at least two conductive fittings, each of which electrically connects a corresponding connection means and fastener.

10. A clasp according to claim 8 in which the gate means is pivotally connected to the body and includes a jam for clamping the second end of material into place when the gate is closed.

11. A clasp according to claim 9 in which each conductive fitting is exposed on the inner side of the clasp so that the fitting may contact the wearer's skin.

12. A clasp for a conductive grounding strap formed of material that has at least two conductive sections on one side, comprising:
   (a) a body;
   (b) at least two connection means, at least one of which is for connecting a first end of the material to the clasp body;
   (c) at least two grounding cord fasteners attached to the clasp body, each of which is electrically connected at all times to a conductive section of the material;
   (d) a passageway formed in the body through which portions of the material may extend; and
   (e) a gate means for adjustably securing a second end of the material in the body so that the second end exits the body with its conductive side facing the first end of material.

13. A clasp according to claim 12 in which each connection means is electrically connected to a corresponding conductive section of the material and which clasp further comprises at least two fittings each of which electrically connects a corresponding connection means and fastener.

14. A clasp according to claim 12 in which the gate means is pivotally connected to the body and includes a jam for clamping the second end of material into place when the gate is closed.

15. A clasp according to claim 13 in which each conductive fitting is exposed on the inner side of the clasp body so that the fitting may contact the wearer's 16. A conductive strap, comprising:
   I. a clasp, comprising:
      (a) a clasp body;
      (b) connection means attached to the clasp body for connecting a first end of a length of material having at least one conductive section to the clasp body, which connection means is electrically connected to the conductive section of the material;
      (c) a grounding cord fastener attached to the clamp body;
      (d) a passageway formed in the body through which portions of the material may extend;
      (e) a gate means pivotally connected to the body and which is openable and closeable to obstruct the passageway adjustably for adjustably securing a second end of the material in the body so that the second end exits the clasp to overlay the first end; and
      (f) a conductive fitting electrically connecting the fastener and the connection means so that the fastener is electrically connected at all times to the conductive section of the material, regardless of whether the gate means is opened or closed; and
   II. a length of material whose first end is connected to the clasps connection means.

17. A conductive grounding strap, comprising:
   I. a clasp, comprising:
      (a) a body;
      (b) at least two connection means, at least one of which is for connecting a first end of the material to the clasp body;
      (c) at least two grounding cord fasteners attached to the clamp body, each of which is electrically connected at all times to a conductive section of the material;
      (d) a passageway formed in the body through which portions of the material may extend; and
      (e) a gate means for adjustably securing a second end of the material in the body so that the second end exits the clasp to overlay the first end; and
   II. a length of material having at least two conductive sections, whose first end is connected to at least one of the clasp's connection means.

* * * * *